United States Patent [19]
Davidson et al.

[11] Patent Number: 5,747,072
[45] Date of Patent: May 5, 1998

[54] ADENOVIRAL-MEDIATED GENE TRANSFER TO SYNOVIAL CELLS IN VIVO

[75] Inventors: Beverly L. Davidson, Howell; Blake J. Roessler, Ann Arbor, both of Mich.

[73] Assignee: University of Michigan, Ann Arbor, Mich.

[21] Appl. No.: 422,655

[22] Filed: Apr. 14, 1995

Related U.S. Application Data

[63] Continuation of Ser. No. 100,646, Jul. 30, 1993, abandoned.

[51] Int. Cl.$^6$ .................. A61K 48/00; C12N 15/09; C12N 15/63
[52] U.S. Cl. .................. 424/93.2; 435/69.5; 435/172.3; 435/320.1; 514/44
[58] Field of Search .................. 435/172.1, 172.3, 435/235.1, 93.2, 69.5, 320.1; 424/93.1, 93.2, 93.21, 93.6, 93.7; 514/44; 536/23.1, 23.5, 24.1

[56] References Cited

PUBLICATIONS

Davidson, Beverly L. et al., "A model system for in vivo gene transfer into the central nervous system using an adenoviral vector." *Nature Genetics.* 3:219–223 (1993).

Dinarello, C.A., "Reduction of inflammation by decreasing production of interleukin–1 or by specific receptor antagonism." *Int. J. Tiss. Reac.* XIV (2)65–75 (1992).

Jaffe, H.A. et al., "Adenovirus–mediated in vivo gene transfer and expression in normal rat liver." *Nature Genetics.* 1:372–378 (1992).

Harris, Edward D., "Excitement in synovium: The rapid evolution of understanding of rheumatoid arthritis and expectations for therapy." *J. Rheumatol. Suppl.* 32:3–5 (1992).

Remmers, Elaine F. et al. "Cytokines and growth regulation of synoviocytes from patients with rheumatoid arthritis and rats with streptococcal cell wall arthritis." *Growth Factors.* 2:179–188 (1990).

Graham and Van Der Eb, "A new technique for the assay of infectivity of human adenovirus 5 DNA." *Virology.* 52:456–467 (1973).

Bodon and Prohaszka, "Isolation of an adenovirus from rabbits with diarrhea." *Acta. Vet. Hung.* 28:247–255 (1980).

Muro–Cacho, Carlos A. et al., "Gene transfer in human lymphocytes using a vector based on adeno–associated virus." *J. of Immunotherapy.* 11:231–237 (1992).

Cassel, Aliza et al., "Retroviral–mediated gene transfer into CD34–enriched human peripheral blood stem cells." *Experimental Hematology.* 21:585–591 (1993).

Roessler and Davidson, "Genetic modification of synoviocytes in vivo using recombinant adenoviral vectors." *Clinical Research* 41(2):171A(1993).

Arend, William P. et al., "Biological properties of recombinant human monocyte–derived interleukin 1 receptor antagonist." *J. Clin. Invest.* 85:1694–1697 (1990).

Koch, Alisa E. et al., "Expression of interleukin–1 and interleukin–1 receptor antagonist by human rheumatoid synovial tissue macrophages." *Clin. Immun. and Immunopathology.* 65:23–29 (1992).

Yocum, David E. et al., "Hyperplastic synoviocytes from rats with streptococcal cell wall–induced arthritis exhibit a transformed phenotype that is thymic–dependent and retinoid inhibitable." *Am. J. of Pathology.* 132:38–48 (1988).

Quantin, B. et al., "Adenovirus as an expression vector in muscle cell in vivo." *Proc. Natl. Acad. Sci.* 89:2581–2584 (1992).

Hurwitz and Chinnadurai, "Evidence that a second tumor antigen coded by adenovirus early gene region E1a is required for efficient cell transformation." *Proc. Natl. Acad. Sci.* 82:163–167 (1985).

Haskill, Stephen et al., "cDNA cloning of an intracellular form of the human interleukin 1 receptor antagonist associated with epithelium." *Proc. Natl. Acad.* 88:3681–3685 (1991).

Bodon, L. et al., "Isolation of an adenovirus from rabbits." Preliminary Report, Veterinary Research Institute. 73–75 (1979).

Bandara et al. 1992 DNA and Eeu Biology 11(3):227–331.
Rosenfeld et al. 1992. Cell 68:143–155.
Berkner. 1989 6:616–629.
Uhlmann et al. 1990 Chemical Reviews 90(4): 544–579.
Carter et al. 1990. nature 344:633–638.
Hannum et al 1990. Nature 343:336–340.
Eisenberg et al. 1990. Nature 343:341–346.

*Primary Examiner*—Brian R. Stanton
*Attorney, Agent, or Firm*—Campbell & Flores LLP

[57] ABSTRACT

This invention provides recombinant adenoviral vectors having an expression control sequence operatively linked to a gene that encodes an anti-inflammatory polypeptide or that produces on transcription an anti-inflammatory ribozyme or antisense RNA molecule. This invention also provides methods of transferring a gene to a synovial cell by transducing the synovial cell in vivo, with a recombinant adenoviral vector. This invention also provides methods of treating an inflammatory condition in the joint of a subject comprising administering to the joint a therapeutically effective amount of a recombinant adenoviral vector having an expression control sequence operatively linked to a gene that encodes an anti-inflammatory polypeptide or that produces on transcription an anti-inflammatory ribozyme or antisense RNA molecule.

2 Claims, 3 Drawing Sheets

SEQUENCE RANGE: 9 to 551

```
        10         20         30         40         50         60
         *          *          *          *          *          *
  AT GGAAATCTCC AGAGGCCTCC GCAGTCACCT AATCACTCTC CTCCTCTTCC
  Met GluIleCys ArgGlyLeu ArgSerHisLeu IleThrLeu LeuLeuPhe>
   a          a TRANSLATION OF IL-1RA [A]         a          >

70         80         90        100        110        120
         *          *          *          *          *          *
  TGTTCCATTC AGAGACGATC TGCCGACCCT CTGGGAGAAA ATCCAGCAAG ATGCAAGCCT
  LeuPheHisSer GluThrIle CysArgPro SerGlyArgLys SerSerLys MetGlnAla>
   a                    TRANSLATION OF IL-1RA [A]         a          >

130        140        150        160        170        180
         *          *          *          *          *          *
  TCAGAATCTG GGATGTTAAC CAGAAGACCT TCTATCTGAG GAACAACCAA CTAGTTGCTG
  PheArgIleTrp AspValAsn GlnLysThr PheTyrLeuArg AsnAsnGln LeuValAla>
   a                    TRANSLATION OF IL-1RA [A]         a          >

190        200        210        220        230        240
         *          *          *          *          *          *
  GATACTTGCA AGGACCAAAT GTCAATTTAG AAGAAAAGAT AGATGTGGTA CCCATTGAGC
  GlyTyrLeuGln GlyProAsn ValAsnLeu GluGluLysIle AspValVal ProIleGlu>
   a                    TRANSLATION OF IL-1RA [A]         a          >

250        260        270        280        290        300
         *          *          *          *          *          *
  CTCATGCTCT GTTCTTGGGA ATCCATGGAG GGAAGATGTG CCTGTCCTGT GTCAAGTCTG
  ProHisAlaLeu PheLeuGly IleHisGly GlyLysMetCys LeuSerCys ValLysSer>
   a                    TRANSLATION OF IL-1RA [A]         a          >

310        320        330        340        350        360
         *          *          *          *          *          *
  GTGATGAGAC CAGACTCCAG CTGGAGGCAG TCAACATCAC TGACCTGAGC GAGAACAGAA
  GlyAspGluThr ArgLeuGln LeuGluAla ValAsnIleThr AspLeuSer GluAsnArg>
   a                    TRANSLATION OF IL-1RA [A]         a          >

370        380        390        400        410        420
         *          *          *          *          *          *
  AGCAGGACAA GCGCTTCGCC TTCATCCGCT CAGACAGTGG CCCCACCACC AGTTTTGAGT
  LysGlnAspLys ArgPheAla PheIleArg SerAspSerGly ProThrThr SerPheGlu>
   a                    TRANSLATION OF IL-1RA [A]         a          >

430        440        450        460        470        480
         *          *          *          *          *          *
  CTGCCGCCTG CCCCGGTTGG TTCCTCTGCA CAGCGATGGA AGCTGACCAG CCCGTCAGCC
  SerAlaAlaCys ProGlyTrp PheLeuCys ThrAlaMetGlu AlaAspGln ProValSer>
   a                    TRANSLATION OF IL-1RA [A]         a          >

490        500        510        520        530        540
         *          *          *          *          *          *
  TCACCAATAT GCCTGACGAA GGCGTCATGG TCACCAAATT CTACTTCCAG GAGGACGAGT
  LeuThrAsnMet ProAspGlu GlyValMet ValThrLysPhe TyrPheGln GluAspGlu>
   a                    TRANSLATION OF IL-1RA [A]         a          >

550
         *
  AGTACTGCCC A
  ***TyrCysPro>
       a    >
```

FIG. 3

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 543 base pairs
( B ) TYPE: nucleic acid
( C ) STRANDEDNESS: double
( D ) TOPOLOGY: linear ( i x ) FEATURE:
( A ) NAME/KEY: CDS
( B ) LOCATION: 1..534

( x i ) SEQUENCE DESCRIPTION: SEQ ID NO:1:

| ATG | GAA | ATC | TGC | AGA | GGC | CTC | CGC | AGT | CAC | CTA | ATC | ACT | CTC | CTC | CTC | 48 |
| Met | Glu | Ile | Cys | Arg | Gly | Leu | Arg | Ser | His | Leu | Ile | Thr | Leu | Leu | Leu | |
| 1 | | | | 5 | | | | | 10 | | | | | 15 | | |

| TTC | CTG | TTC | CAT | TCA | GAG | ACG | ATC | TGC | CGA | CCC | TCT | GGG | AGA | AAA | TCC | 96 |
| Phe | Leu | Phe | His | Ser | Glu | Thr | Ile | Cys | Arg | Pro | Ser | Gly | Arg | Lys | Ser | |
| | | | 20 | | | | | 25 | | | | | 30 | | | |

| AGC | AAG | ATG | CAA | GCC | TTC | AGA | ATC | TGG | GAT | GTT | AAC | CAG | AAG | ACC | TTC | 144 |
| Ser | Lys | Met | Gln | Ala | Phe | Arg | Ile | Trp | Asp | Val | Asn | Gln | Lys | Thr | Phe | |
| | | 35 | | | | | 40 | | | | | 45 | | | | |

| TAT | CTG | AGG | AAC | AAC | CAA | CTA | GTT | GCT | GGA | TAC | TTG | CAA | GGA | CCA | AAT | 192 |
| Tyr | Leu | Arg | Asn | Asn | Gln | Leu | Val | Ala | Gly | Tyr | Leu | Gln | Gly | Pro | Asn | |
| | 50 | | | | | 55 | | | | | 60 | | | | | |

| GTC | AAT | TTA | GAA | GAA | AAG | ATA | GAT | GTG | GTA | CCC | ATT | GAG | CCT | CAT | GCT | 240 |
| Val | Asn | Leu | Glu | Glu | Lys | Ile | Asp | Val | Val | Pro | Ile | Glu | Pro | His | Ala | |
| 65 | | | | | 70 | | | | | 75 | | | | | 80 | |

| CTG | TTC | TTG | GGA | ATC | CAT | GGA | GGG | AAG | ATG | TGC | CTG | TCC | TGT | GTC | AAG | 288 |
| Leu | Phe | Leu | Gly | Ile | His | Gly | Gly | Lys | Met | Cys | Leu | Ser | Cys | Val | Lys | |
| | | | | 85 | | | | | 90 | | | | | 95 | | |

| TCT | GGT | GAT | GAG | ACC | AGA | CTC | CAG | CTG | GAG | GCA | GTT | AAC | ATC | ACT | GAC | 336 |
| Ser | Gly | Asp | Glu | Thr | Arg | Leu | Gln | Leu | Glu | Ala | Val | Asn | Ile | Thr | Asp | |
| | | | 100 | | | | | 105 | | | | | 110 | | | |

| CTG | AGC | GAG | AAC | AGA | AAG | CAG | GAC | AAG | CGC | TTC | GCC | TTC | ATC | CGC | TCA | 384 |
| Leu | Ser | Glu | Asn | Arg | Lys | Gln | Asp | Lys | Arg | Phe | Ala | Phe | Ile | Arg | Ser | |
| | | 115 | | | | | 120 | | | | | 125 | | | | |

| GAC | AGT | GGC | CCC | ACC | ACC | AGT | TTT | GAG | TCT | GCC | GCC | TGC | CCC | GGT | TGG | 432 |
| Asp | Ser | Gly | Pro | Thr | Thr | Ser | Phe | Glu | Ser | Ala | Ala | Cys | Pro | Gly | Trp | |
| | 130 | | | | | 135 | | | | | 140 | | | | | |

| TTC | CTC | TGC | ACA | GCG | ATG | GAA | GCT | GAC | CAG | CCC | GTC | AGC | CTC | ACC | AAT | 480 |
| Phe | Leu | Cys | Thr | Ala | Met | Glu | Ala | Asp | Gln | Pro | Val | Ser | Leu | Thr | Asn | |
| 145 | | | | | 150 | | | | | 155 | | | | | 160 | |

| ATG | CCT | GAC | GAA | GGC | GTC | ATG | GTC | ACC | AAA | TTC | TAC | TTC | CAG | GAG | GAC | 528 |
| Met | Pro | Asp | Glu | Gly | Val | Met | Val | Thr | Lys | Phe | Tyr | Phe | Gln | Glu | Asp | |

GAG TAGTACTGCC CA                                                        543
Glu ( 2 ) INFORMATION FOR SEQ ID NO:2:

( i ) SEQUENCE CHARACTERISTICS:
        ( A ) LENGTH: 177 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met Glu Ile Cys Arg Gly Leu Arg Ser His Leu Ile Thr Leu Leu Leu
 1               5                  10                  15
Phe Leu Phe His Ser Glu Thr Ile Cys Arg Pro Ser Gly Arg Lys Ser
            20                  25                  30
Ser Lys Met Gln Ala Phe Arg Ile Trp Asp Val Asn Gln Lys Thr Phe
        35                  40                  45
Tyr Leu Arg Asn Asn Gln Leu Val Ala Gly Tyr Leu Gln Gly Pro Asn
    50                  55                  60
Val Asn Leu Glu Glu Lys Ile Asp Val Val Pro Ile Glu Pro His Ala
65                  70                  75                  80
Leu Phe Leu Gly Ile His Gly Gly Lys Met Cys Leu Ser Cys Val Lys
                85                  90                  95
Ser Gly Asp Glu Thr Arg Leu Gln Leu Glu Ala Val Asn Ile Thr Asp
            100                 105                 110
Leu Ser Glu Asn Arg Lys Gln Asp Lys Arg Phe Ala Phe Ile Arg Ser
        115                 120                 125
Asp Ser Gly Pro Thr Thr Ser Phe Glu Ser Ala Ala Cys Pro Gly Trp
    130                 135                 140
Phe Leu Cys Thr Ala Met Glu Ala Asp Gln Pro Val Ser Leu Thr Asn
145                 150                 155                 160
Met Pro Asp Glu Gly Val Met Val Thr Lys Phe Tyr Phe Gln Glu Asp
                165                 170                 175
Glu
```

ADENOVIRAL-MEDIATED GENE TRANSFER TO SYNOVIAL CELLS IN VIVO

This application is a continuation of application Ser. No. 08/100,646, filed Jul. 30, 1993, now abandoned.

BACKGROUND OF THE INVENTION

This invention relates to the field of genetic engineering and, in particular, to methods of transducing synovial cells in vivo via adenoviral-mediated transduction.

Among acquired autoimmune conditions are the inflammatory arthropathies, a heterogeneous group of diseases that, in the case of rheumatoid arthritis alone, affects at least 1% of the population. In general, these diseases are characterized by abnormal proliferation of the specialized epithelial cells known as synoviocytes that form the lining tissue of the intra-articular space of diarthrodial (synoval, freely moving) joints. Based upon morphological and functional criteria, synoviocytes have been characterized as type A (also referred to as type I) or type B (also referred to as type II). Type A synoviocytes are presumably derived from macrophage/monocyte precursors, exhibit phagocytic activity and may function as antigen presenting cells. Type B cells are more fibroblast-like in appearance and are associated with the production of hyaluronic acid and other components of joint fluid.

Alterations in the normal biology of the synoviocytes are important in the development and maintenance of the pathologic process associated with rheumatoid arthritis, including invasion and destruction of articular cartilage and bone. In addition to the production of elastase and collagenase, synoviocytes mediate this pathophysiologic process by producing and up-regulating the expression of cell surface proteins important in the recruitment and activation of lymphocytes and macrophages within rheumatoid synovium.

Currently, the treatments available for rheumatoid arthritis are associated with significant untoward side effects and are largely ineffective in preventing the destruction of articular cartilage and bone associated with erosive articular disease. Increasing evidence points to the pathophysiologic role of synoviocytes in rheumatoid arthritis. Synoviocytes are thought to mediate pathological processes by the persistence of a semi-transformed phenotype, the expression and secretion of collagenase, elastase and other metalloproteinases capable of degrading cartilage and bone matrices, and the expression of pro-inflammatory cytokines.

Although synoviocytes produce many effector molecules associated with the pathogenesis and pathophysiology of rheumatoid arthritis, IL-1 functions as a central mediator of inflammation. Many studies have elucidated the importance of regional IL-1 production in the generation and maintenance of synovial inflammation. Thus the ability to specifically block IL-1 activity within anatomically defined regions of inflamed synovium is a desirable therapeutic goal.

Gene therapy is gaining wider use in the treatment of disease. Frequently genes are introduced into cells by retroviral-mediated transduction. However, the efficiency of gene transfer into synoviocytes with retroviruses is relatively low and the process is laborious.

There thus exists a need for methods to prevent or alleviate inflammatory conditions in synovial joints and to endow synoviocytes with the ability to express transferred genes encoding anti-inflammatory agents. However, to date, the art has not reported the successful transduction of synoviocytes in vivo. This invention satisfies these needs by providing methods of producing transduced synoviocytes that express transferred genes.

SUMMARY OF THE INVENTION

This invention provides recombinant adenoviral vectors having an expression control sequence operatively linked to a gene that encodes an anti-inflammatory polypeptide or that produces on transcription an anti-inflammatory ribozyme or antisense RNA molecule.

This invention also provides methods of transferring a gene to a synovial cell by transducing the synovial cell in vivo, with a recombinant adenoviral vector having an expression control sequence operatively linked to the gene.

This invention also provides methods of treating an inflammatory condition in the joint of a subject comprising administering to the joint a therapeutically effective amount of a recombinant adenoviral vector having an expression control sequence operatively linked to a gene that encodes an anti-inflammatory polypeptide or that produces on transcription an anti-inflammatory ribozyme or antisense RNA molecule.

BRIEF DESCRIPTION OF THE DRAWINGS

FIGS. 1A–1G show photographs of rabbit knees 1–8 weeks post-infection with AdCMVlacZ. FIGS. 1C–1F show samples of periarticular synovial tissues reacted with X-gal and embedded in glycomethracrylate. 5 μm sections were mounted onto glass slides, counterstained with hematoxylin/eosin and examined by light microscopy. Dark staining cells were present with vascular synovial villi (FIG. 1C), synovium covering adipose tissue (FIG. 1D), synovium overlying bone (FIG. 1E) and at the junction of synovium with articular cartilage (FIG. 1F). Microscopic examination confirmed that lacZ expressing cells were confined to the first several layers of cells present within the synovium consistent with the known location of synoviocytes in rabbits. (p=patella, t=tendon, a=adipose tissue, c=cartilage, b=bone)

FIG. 3 depicts the nucleotide sequence and deduced amino acid sequence of the IL-1 receptor antagonist gene [SEQ ID NO: 1].

DETAILED DESCRIPTION OF THE INVENTION

This invention provides therapeutic methods for the treatment of joint disease. These methods involve introducing recombinant genes encoding anti-inflammatory agents into synovial cells of joints in vivo. The cells produce the anti-inflammatory agents which subsequently alleviate inflammation in the joint. Thus, this invention provides a gene therapy for inflammatory arthropathies such as osteoarthritis and rheumatoid arthritis.

The methods of this invention involve the use of recombinant adenoviral vectors for mediating the introduction of genes into synovial cells. The recombinant adenoviral vectors of this invention produce superior results to other vectors in the transfer of genes to the synovium. Retroviral-mediated transduction requires cell division for the integration of the viral genome. Since synovial cells grow slowly, it is more difficult to obtain as high a level of transduction with retroviruses as with adenoviruses, which transduce relatively quiescent cells.

Recombinant adenoviral vectors also find use for the transduction of synovial cells in vitro. These transduced cells are useful in the production of recombinant protein.

The recombinant adenoviral vectors of this invention have an expression control sequence operatively linked to a gene. The adenoviral vectors of this invention are "recombinant" in that the gene and either the adenoviral sequences or the expression control sequence are from a different original source and are not naturally attached together. The term "adenoviral vector" refers to adenoviral DNA molecules that can mediate the transfer of the gene into the host cell.

As used herein, the term "expression control sequence" refers to a nucleic acid sequence that regulates the expression of a gene to which it is operatively linked. An expression control sequence is "operatively linked" to a gene when the expression control sequence controls and regulates the transcription and, as appropriate, translation of the gene. The term "operatively linked" includes the provision of an appropriate start codon (i.e., ATG), in front of a polypeptide-encoding gene and maintenance of the correct reading frame of that gene to permit proper translation of the mRNA.

This invention contemplates the use of both constitutive and inducible expression control sequences. The Rous Sarcoma Virus ("RSV") promoter finds use in this invention as part of an expression control sequence. The RSV promoter is commonly used in the art for the expression of recombinant genes. (Gorman et al., *Molec. and Cell Biol.* 2:1044 (1982).) One can construct other expression control sequences by combining promoter and enhancer elements. Useful promoters include those which can promote tissue specific gene expression or enhanced persistence of trans-gene expression in the transduced cell. Examples include the β-actin promoter, stromelysin promoter, the IL-1 promoter, NF-κB promoter, HPRT promoter and α-1 antitrypsin promoter. Many of these regulatory sequences can be obtained through the use of polymerase chain reaction (PCR) using specific synthetic oligonucleotide primers based upon published sequence information. The cytomegalovirus (CMV) enhancer also finds use in the expression control sequences of this invention. One skilled in the art can identify other useful expression control sequences empirically.

Nucleic acid sequences that regulate the translation of a gene, such as the SV40 polyadenylation sequence, also find use in this invention.

As used herein, the term "gene" refers to a sequence of nucleotides that encodes a polypeptide or that produces on transcription a ribozyme or an antisense nucleic acid molecule. Rybozymes are catalytic RNA molecules that cleave other RNA molecules having particular nucleic acid sequences. Antisense nucleic acid molecules are nucleic acid molecules that have nucleotide sequences complementary to particular mRNA molecules of the sense strand of genes. Antisense nucleic acid molecules hybridize to and interfere with the transcription or translation of a complementary DNA or mRNA molecule. Given the DNA sequence of a gene, a person of skill in the art knows how to make ribozymes and antisense nucleic acid molecules that interfere with transcription or translation of the gene. (See e.g., Weintraub, *Sci. Am.* 262:40–46 (January 1990); Marcus-Sekura, *Anal. Biochem.* 172:289–95 (1988); and Hasselhoff et al., *Nature* 334:585–591 (1988).)

In one embodiment of this invention, the recombinant adenoviral vector includes a gene that encodes an anti-inflammatory polypeptide or produces on transcription an anti-inflammatory ribozyme or antisense RNA molecule. As used herein, "anti-inflammatory" refers to a polypeptide, ribozyme or antisense nucleic acid molecule that inhibits or reduces an inflammatory condition in a diarthrodial joint.

Interleukin-1β ("IL-1β") is a protein mediator of inflammation. Therefore, IL-1 antagonists are anti-inflammatory agents. In particular, the IL-1 receptor antagonist is a potent anti-inflammatory agent. This invention provides products and processes using a gene that encodes this polypeptide.

Soluble forms of receptors involved in the inflammatory process also act as anti-inflammatory agents. For example, soluble versions of VCAM-1, the IL-1 receptor and the IL-6 receptor, secreted by a synoviocyte into the synovial space, compete with cell-bound receptors for their ligands and inhibit inflammatory processes dependent upon ligand binding. Accordingly, genes that encode soluble forms of these receptors find use in this invention.

Synovial cells produce metallo-proteinases, such as collagenase and elastase, that are involved in the destruction of the synovium. Genes for inhibitors of these enzymes find use in this invention.

Genes producing on transcription ribozymes or antisense RNA molecules that inhibit the expression of VCAM-1, IL-1 receptor, IL-6 receptor and metallo-proteinases also find use in this invention.

This invention also provides methods of transferring a gene into a synovial cell by introducing into a synovial cell in vivo, by means of adenoviral-mediated transduction, a recombinant adenoviral vector having an expression control sequence operatively linked to the gene.

This invention provides methods of treating an inflammatory condition in the joint of a subject comprising the step of administering a therapeutically effective amount of a recombinant adenoviral vector of this invention to the subject. As used herein, the term "therapeutically effective amount" is that amount necessary to alleviate the condition from which the subject suffers or to prevent or delay the onset or recurrence of symptoms. As used herein, the term "subject" includes mammals or humans.

In the practice of the therapeutic methods of this invention, a therapeutically effective amount of a recombinant adenoviral vector of this invention is administered so as to allow contact between the adenoviruses and the synovial cells. A preferred method is to introduce the adenoviral vector into the synovial space of the inflamed joint. Administration by intra-articular injection is preferred because it provides superior access to the joint by the therapeutic agent.

The recombinant adenoviral vectors are administered in an acceptable carrier. An acceptable carrier is one tolerated by the joint without adverse reaction, such as increased inflammation. Acceptable carriers include, e.g., sterile, distilled water and sterile phosphate buffered saline (PBS).

The particular amount of recombinant adenoviral vector to be administered to the subject will depend on a variety of considerations including the nature of the disease, the severity thereof, the schedule of administration, the age and physical characteristics of the subject, and so forth. Proper dosages may be established using clinical approaches familiar to the medicinal arts. Dosages include about $10^7$ to $10^{13}$ particles of viral vector per ml of carrier. The volume administered will vary with the size of the joint. According to one embodiment of this invention, approximately $10^{10}$ adenoviral particles suspended in about 1 ml of sterile PBS constitute a therapeutically effective amount.

EXAMPLE I

Adenoviral Mediated Gene Transfer to Rabbit Synovium in vivo

Replication defective adenoviral vectors are deleted of sequences spanning E1A, E1B, and a portion of the E3 region, impairing the ability of this virus to replicate or transform non-permissive cells. (Hurwitz, et al., *Proc. Natl. Acad. Sci. U.S.A.* 82:163–167 (1985).) In the vector AdCMVlacZ, the early enhancer/promoter of the cytomegalovirus was used to drive transcription of lacZ with an SV40 polyadenylation sequence cloned downstream from this reporter. An identically derived Ad5 adenoviral vector, AdCSV, was used as a control. AdCSV does not contain the gene for *E. coli* β-galactosidase. AdCMVlacZ is functionally identical to AdRSVIRAP, infra, except, that AdRSVIRAP uses the RSV promoter to drive transcription of the IL-1ra gene.

High titer recombinant adenovirus was prepared by amplification in LE293 cells using established methods. (Graham et al., (1973).) Virus was purified from cell lysates by cesium chloride gradient ultra-centrifugation followed by de-salting on Sephadex G-50 (Sigma Biochemicals, St. Louis, Mo.) column in PBS. Purified virus was used immediately for intra-articular injections. Titers (particles/ml) were determined by $O.D._{260}$, and were approximately $1 \times 10^{13}$ particles/ml±one log (1.0 O.D. unit equals $1.0 \times 10^{12}$ particles/ml).

Male New Zealand white rabbits 2 kg in weight were used for these experiments. Prior to the procedure rabbits were anesthetized with a single intramuscular dose of ketamine/xylazine (25 mg/kg ketamine, 5 mg/kg xylazine), and the area surrounding both hind knees was shaved and prepared with povidone/iodine. Using sterile technique and a medial approach, 1 ml of purified AdCMVlacZ suspended in PBS was infused into the intra-articular space of the right knee over a period of 30 seconds. The left knee was either left uninjected (N=3 rabbits) or was prepared in an identical manner and injected with the control vector AdCSV (N=4 rabbits).

At 1 to 8 week intervals post infection, animals were euthanized with an intravenous overdose of pentobarbital. Both hind knees were infused with 10 ml of 2% paraformaldehyde in piperazine-N,N'-bis[2-ethansulfonic acid] (Pipes) pH 6.9. Knee joints were removed en bloc, the intra-articular space exposed by sharp dissection and samples immersed in the same fixative for an additional 1 hour at 4° C. Samples were washed twice in PBS/2 mM $MgCl_2$, and reacted in 5 mM $K_3Fe(CN)_6$, 2 mM $MgCl_2$, 0.01% sodium deoxycholate, 0.02% NP-40 and 1 mg/ml 5-bromo-4-chloro-3-indolyl-b-D-galactoside ("X-gal") in PBS for 30 min at 37° C. (Walsh and Cepko, 1988). The intra-articular spaces were then widely exposed by dissection, inspected visually and photographed en fosse using a stereoscopic dissecting microscope (Nikon). See FIG. 1.

Tissues stained with X-gal were processed for routine histology or electron microscopy by postfixing in 2% glutaraldehyde/PBS. Samples containing bone were decalcified by treatment with 25% formic acid/7.5% sodium citrate, neutralized in 5% sodium sulfate, and further fixed in 2% glutaraldehyde/PBS. Samples were embedded in glycomethacrylate, and 5 mm sections were cut using a microtome, mounted onto glass slides and counterstained with hematoxylin/eosin. Samples for electron microscopy were post fixed in 2% glutaraldehyde, 1.5% paraformaldehyde, and 0.0015% $CaCl_2$ in 0.1M Na cacodylate followed by 1% osmium tetroxide in 0.1M Na cacodylate containing 5% sucrose. Samples were then dehydrated in ethanol and embedded in Spurr's medium using previously described methods. (Davidson et al., *Nature Genetics* 3:219–223 (1993).) Articular and periarticular tissues from control knees were processed identically for both light and electron microscopy.

Samples for immunohistochemical staining were prepared by isolation of the synovial membrane by sharp dissection and fresh freezing in the cryoprotective mounting medium, O.C.T. (Miles Inc., Elkhart, Ind.). Sections (6 mm) were prepared on a Bright cryostat and placed onto poly-L-lysine coated slides. Slides were post fixed in methanol at −20° C. and blocked by incubation in 1% BSA (Bovine Serum Albumin)/PBS for 1 hour at 20° C. Slides were then incubated for 1 hour with biotin conjugated to monoclonal (mouse) anti-β-galactosidase (Sigma), rinsed 3 times in PBS and reacted with avidin-AMCA (Vector Labs, Burlingame, Calif.) for 1 hour at 20° C. Sections of infected synovium were also reacted with antibodies to adenoviral structural proteins. Incubations were performed for 1 hour at room temperature with FITC (fluoro-iso-thio-cyanate) conjugated goat anti-hexon (Biodesign International, Kennebunkport, Me.) or monoclonal (murine) anti-adenoviral coat protein (BioGenex Laboratories, San Ramon, Calif.), followed by incubation with FITC conjugated goat anti-murine IgG (Vector Labs). After rinsing in PBS, slides were examined and photographed using fluorescent microscopy following excitation with light at 350 nm (AMCA) or 492 nm (FITC). Light field photomicrographs were routinely taken of the same fields using Nomarski optics.

Serum was obtained from rabbits prior to intra-articular infection and then at serial time points post-infection. These samples were used to detect circulating antibodies directed against recombinant adenoviral structural proteins as well as *E. coli* β-galactosidase. Aliquots of total viral protein (1 μg) obtained from purified preparations of AdBglII (a recombinant Ad5 derivative that lacks transgene sequences), and aliquots of *E. coli* β-galactosidase (1 μg, Sigma) were electrophoresed on 12% polyacrylamide gels containing 1% SDS and then transferred to polyvinylidenefluoride (PVDF) (Millipore Corp., Bedford, Mass.) membranes using a semi-dry electrophoretic transfer apparatus (Hoefer Scientific Instruments, San Francisco, Calif.). AdBglII was purified by double banding through cesium chloride gradients using standard techniques. (Stoolman et al., *Blood* 70:1842–1850 (1987).) Membranes were blocked by incubation with 1% non-fat dry milk in Tris buffered saline (TBS, pH 8.0) for 1 hour and then reacted with serum obtained from the cohort of experimental rabbits (1:100 dilution in tris-buffered saline, 0.05% Tween-20 ("TBS/T").

Membranes were washed twice in TBS/T and incubated with goat anti-rabbit secondary antibodies conjugated to horseradish peroxidase (1:2000 in TBS/T; Kirkegaard & Perry Laboratories, Gaithersburg, Md.). Following two washes in TBS, and one wash in PBS, membranes were incubated in ECL ("enhanced chemiluminescence") reagent (Amersham Corp., Arlington Heights, Ill.) for 1 minute, rinsed, and autoradiographed. The identity and size of adenoviral structural and non-structural proteins recognized by cross reactive antibodies present in the serum samples was determined.

Visual examination of the intra-articular surfaces of knees injected with the vector AdCMVlacZ showed extensive expression of β-galactosidase throughout the synovial tissues at 1 week and up to 8 weeks post administration of AdCMVlacZ. Contralateral control joints that were uninfected or infected with an Ad5 vector that did not contain the gene for β-galactosidase showed no evidence of blue staining cells at 1 week or throughout the experimental period. Qualitatively, the number of lacZ expressing cells throughout the synovium progressively declined from 1 week to 8 weeks post infection. The number of synoviocytes expressing lacZ activity at 8 weeks was estimated to be approximately 25% of that observed at 1 week post-injection. Alternative explanations for the progressive decline in lacZ expression observed in vivo include animal to animal variation, alterations in the transcriptional activity of the CMV promoter, direct toxicity of the transgene product, or the development of a neutralizing immune response.

Synovial lining cells form a serosal surface that covers multiple types of subsynovial tissue. (Barland et al., *J. Cell Biol.* 14:207–220 (1962); Krey et al., *Arthritis Rheum.* 14:319–341 (1971); and Pitsillides et al., *Ann. Rheum. Dis.* 51:992–995 (1992).) Routine histologic examination of articular and periarticular tissues obtained 1 week post infection with AdCMVlacZ showed X-gal staining cells present within vascular synovial villi, as well as in the synovial tissue covering tendons, bone, articular cartilage, and subsynovial adipose tissue. The cells expressing lacZ activity were synoviocytes as evidenced by typical location and morphologic appearance. Blue staining cells were confined to the first two to three cell layers in articular and periarticular regions, areas that correspond to the known distribution of synoviocytes in rabbits. (Krey et al., *Arthritis Rheum.* 16:324–340 (1973); and Lever et al., *Anat. Rec.* 132:525–537 (1958).)

Type A synoviocytes are thought to be derived from cells of monocyte/macrophage lineage and therefore may produce significant endogenous levels of lysosomal galactosidase, an enzyme that may react with the X-gal substrate and produce false-positive signals. Specific expression of transgenic *E. coli* lacZ as opposed to endogenous galactosidase activity was confirmed in the infected synoviocytes by immunohistochemical staining using a monoclonal antibody to *E. coli* β-galactosidase. Periarticular tissues harvested at 3 weeks post infection with AdCMV-lacZ continued to show evidence for the specific expression of *E. coli* β-galactosidase whereas control samples did not.

In order to identify the lacZ expressing cells as type A or B synoviocytes, transmission electron microscopy (TEM) was performed on infected synovial tissue. Previous studies have shown that TEM can be used to identify the type A and type B synoviocytes in rabbits based on a typical ultrastructural appearance. (Steinberg et al., *Scanning. Microsc.* 4:987–1019 (1990).) Additionally, X-gal reaction precipitate can be specifically identified within genetically transduced cells where it appears as dark staining cytoplasmic and perinuclear granules or spicules. (Davidson et al., *Nature Genetics* 3:219–223 (1993); and Engelhardt et al., *Proc. Natl. Acad. Sci. U.S.A.* 88:11192–11196 (1991).) Transmission electron photomicrographs of the periarticular tissues stained with X-gal showed intra-cellular accumulations of X-gal reaction product within both type A and type B rabbit synoviocytes. Both type A synoviocytes, with the characteristic multiple villi and macrophage-like appearance, and type B synoviocytes, more fibroblast-like in appearance, contained the electron dense granules indicative of β-galactosidase activity. Control tissues infected with AdCSV showed no intracellular precipitates. Additionally, the ultrastructural appearance of both type A and type B synoviocytes was normal in rabbits infected with AdCMV-lacZ or AdCSV and no intranuclear inclusion bodies were observed.

A potential concern with the use of adenoviral vectors is the development of a humoral immune response by the host animal. In order to address this possibility, experiments were performed on sera obtained from the entire experimental cohort (n=7 animals) pre- and post-intra-articular infection with adenoviral vectors. Sera was analyzed by Western blot for the development of antibodies to structural proteins of AdCMVlacZ as well as to *E. coli* β-galactosidase. Low titers of antibodies reactive against several adenoviral structural proteins of Ad5 serotype vector AdBglII were present in the preimmune sera obtained from all of the experimental animals. Increases in the titer of pre-existing antibodies, as well as the development of novel antibodies directed against additional adenoviral structural proteins, occurred over the time course of the experiment. Sera from the infected animals consistently cross-reacted with hexon, penton base, hexon associated, and vertex region proteins. (Pettersson, U., *In The Adenoviruses*, H. S. Ginsburg, editor, Plenum Press, New York, 205–229 (1984).) Cross reactive antibodies to other adenoviral proteins, such as the 72 kD DNA binding protein, the fiber, and the core proteins were present in sera obtained from some but not all of the experimental rabbits. In addition, antibodies directed against *E. coli* β-galactosidase were observed in one animal in both pre- and post-immune sera.

EXAMPLE II

Figure 1A:
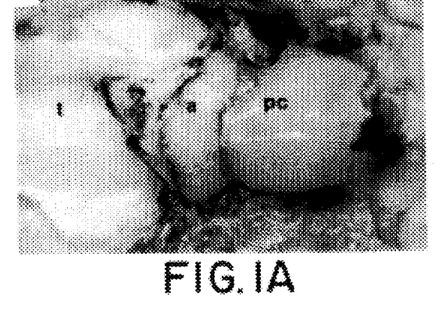
FIG. 1A is a view of the peripatellar synovial tissues 1 week post-infection. Extensive regions of dark staining cells are evident within synovial tissue covering tendons, adipose tissue, and pericondylar regions (10×).
Figure 1B:
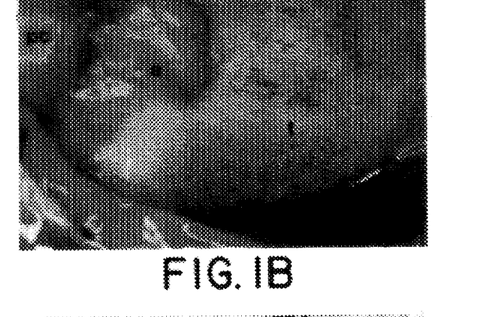
FIG. 1B shows dark staining cells within synovial tissue covering the surface of the patellofemoral tendon 8 weeks post injection.
Figure 1C:
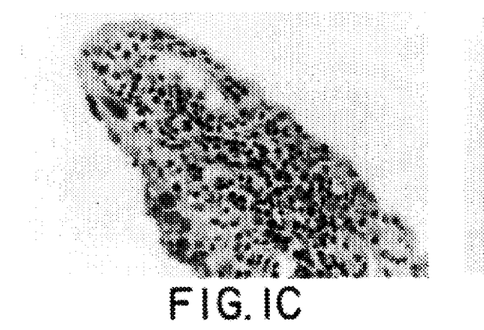
Figure 1D:
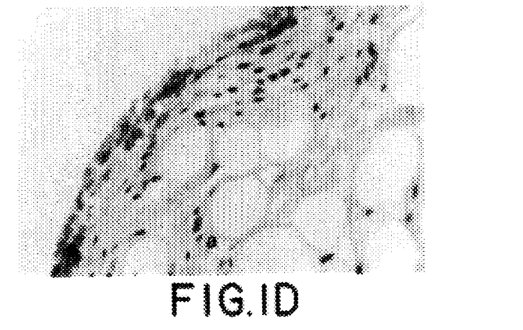
Figure 1E:
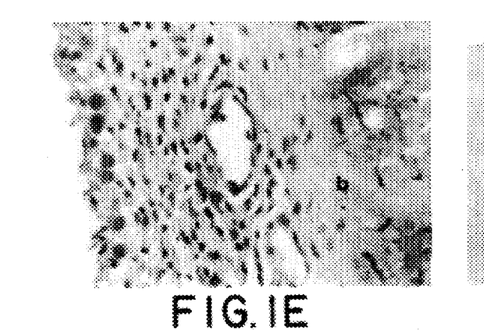
Figure 1F:
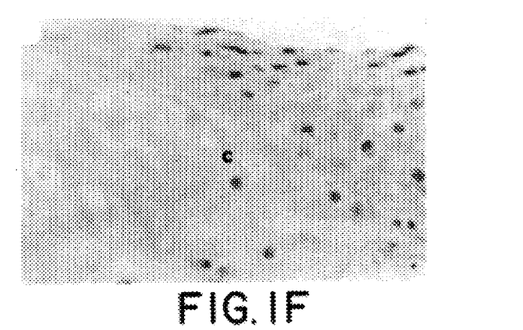
Figure 1G:
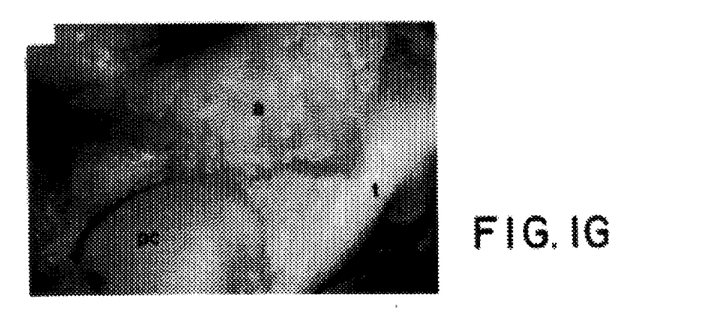
FIG. 1G shows control tissues obtained from the contralateral knee of the same animal that show no dark staining cells (10×).
Figure 2:
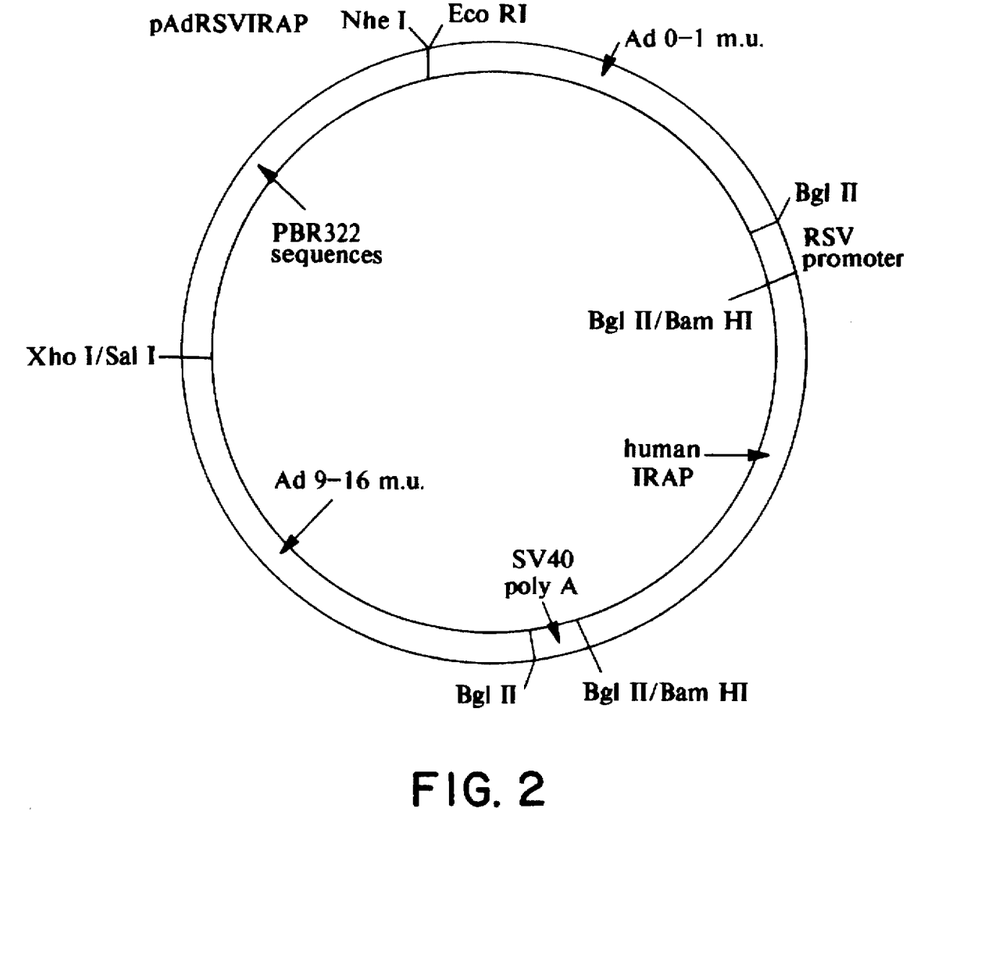
FIG. 2 depicts a map of pAdRSVIRAP.

Intra-articular expression of Human Interleukin Receptor Antagonist Protein using a Recombinant Adenoviral Vector The vector AdRSVIRAP was constructed for use in these studies. FIG. 2 depicts a map of AdRSVIRAP. The map refers to the following functional regions. "Ad 0–1 m.u." refers to adenoviral sequences from 0 to 1 map units, derived from Adenovirus serotype 5. "RSV promoter" refers to the Rous Sarcoma Virus promoter, derived from pREP8, but obtainable from many sources. "Human IRAP" refers to the human IRAP gene, whose sequence is given in FIG. 3 [SEQ ID NO: 1]. "SV40 poly A" refers to the SV40 polyadenylation sequence. "Ad 9–16" refers to adenoviral sequences from 9 to 16 map units derived from Adenovirus serotype 5. "PBR322 sequences" refers to pBR322 sequences containing the bacterial origin of replication and the ampicillin resistance gene. A description of how this vector was constructed follows. However, it should be understood that functional parts may be obtained from a variety of sources to construct an identical vector or one having equivalent function.

This plasmid was constructed as follows. The genomic DNA of human Adenovirus serotype 5 was isolated using standard techniques. Adenovirus serotype 5 can be isolated from bodily fluids by the methods described in Graham et al., *Virology* 52:456–467 (1973). This virus also is generally available within the scientific community. It was then digested with BglII. The fragment containing genomic DNA from 0–1 map units of the adenoviral genome was then cloned into the EcoRI and BglII sites of the shuttle vector pAT153. Plasmid pAT153 is derived from pBR322 and contains the gene for ampicillin resistance and bacterial origin of replication. This produces plasmid pAT153A0–1.

Next, the genomic fragments from 9.2–16.1 map units of the adenoviral genome were isolated. This fragment was cloned into the BglII and SalI sites present in pAT153A0–1. The resulting plasmid retains the single BglII site for further cloning and is designated AdBglII. This results in a replication defective adenoviral vector containing a recombinant adenovirus genome from which sequences for the E1a, E1b and part of E3 regions (XbaI to ClaI have been removed.

This plasmid was subsequently modified to create pADRSV4 as follows. pREP8 (Invitrogen, La Jolla, Calif.) was digested with NotI and KpnI, the ends were filled in with Klenow and the plasmid was re-ligated to form pREPN1. Next, a DNA fragment containing the RSV (Rous Sarcoma virus) promoter, an intervening polylinker (BamHI, XhoI and NotI sites) and the SV40 polyadenylation signal was isolated from the plasmid pREPN1 by digesting the plasmid with XbaI and NruI. This fragment was modified with restriction site linkers (BglII) and then cloned into the BglII site present in the plasmid pAdBglII in order to form the plasmid pAdRSV4. Alternatively, one can obtain sequences encoding the RSV promoter and SV40 polyadenylation site from other commercial sources or by PCR. A combination of restriction endonuclease mapping and dideoxynucleotide sequencing were used to verify the orientation of the fragments in pAdRSV4.

The cDNA for human IL-1ra was obtained as a gift from Immunex (Seattle, Wash.) in the form of a plasmid. The sequence of this cDNA fragment was confirmed by dideoxynucleotide sequencing and comparison with previously published data. Alternatively, one can obtain a DNA molecule encoding IL-1ra by using the published sequence data to make sense and antisense oligonucleotide primers of approximately 30 nucleotides in length that would correspond to the first several amino acids of the coding region. The DNA sequence encoding IL-1 receptor antagonist is provided in FIG. 3 [SEQ ID NO: 1]. The antisense primer can contain the sequence corresponding to the last 10 amino acids of the coding region. The entire coding region of human IL-1ra can then be generated using polymerase chain reaction amplification. Human monocytoid cells (u937; ATCC catalog #CRL 1593) are used for isolation of whole cell RNA using standard methods. (Sambrook et al., *In: A Laboratory Manual*, Cold Spring Harbor Laboratory, Cold Spring Harbor, N.Y., (1989).) The RNA is reverse-transcribed using oligo dT oligonucleotides and reverse transcriptase. Then the single stranded cDNA is used as a template for PCR amplification using the IL-1ra specific primers. Then the PCR generated fragment is isolated from LMP agarose and ends are filled in using Klenow fragment. This DNA fragment is then used for cloning.

The fragment (1.2 kbp) containing the IL-1ra cDNA was excised, blunt-ended and filled in with Klenow. Restriction site linkers (BclII) were attached and this fragment was then cloned into the BamHI site of pAdRSV4. This yielded the plasmid pAdRSVIRAP. A combination of restriction endonuclease mapping and dideoxynucleotide sequencing were used to verify the orientation of the human IL-1ra cDNA fragment within pAdRSVIRAP.

The human adenovirus serotype 5 mutant designated sub360 was used. (Logan et al., *Proc. Natl. Acad. Sci. USA* 81:3655-3659 (1984).) Large quantities of the virus were produced in a biosafety level 2 facility. Genomic DNA was then isolated from the virus and purified using standard methods. Samples of genomic DNA were then digested with both XbaI and ClaI. This removes E1a and E1b sequences. Other vectors are being generated using genomic DNA isolated from the strain dl7001 or from other mutant or wild type human adenoviruses.

Purified plasmid DNA from pAdRSVIRAP was digested with NheI. This DNA was combined with the purified and digested sub360 genomic DNA, and the DNA mixture was transfected using standard calcium chloride transfection procedures into recipient 293 cells (ATCC #CRL 1573. After twenty four hours transfected 293 cell cultures were overlayed with soft agar. These were examined at ten days for the formation of lytic plaques. The plaques were isolated and used to infect fresh 293 cells and large quantities of these viruses were isolated. Genomic DNA from these plaques was analyzed by restriction endonuclease mapping to verify that they contained the cDNA for IL-1ra. The clone AdRSVIRAP contained the cDNA for human IL-1ra in the proper orientation and was a result of a homologous recombinational event.

The identity of recombinant clones was verified by restriction analysis of viral DNA minipreps. Control viruses for in vitro and in vivo experiments were AdBglII (an identical Ad5 derived adenoviral vector that does not contain a functional transgene) and AdRSVlacZ (contains the gene for *E. coli* β-galactosidase). High titer suspensions of recombinant adenovirus were prepared by amplification in 293 cells using a modification of established methods. (Graham et al., *Virology* 52:456–467 (1973).)

The ability of the virus AdRSVIRAP to infect human synoviocytes and to mediate the expression of human IL-1ra was determined in vitro. Human type B synoviocytes were obtained from surgical specimens at the time of elective prosthetic joint replacement. Explanted synoviocytes were characterized phenotypically by the use of a [14C]-glucosamine to [14C]hyaluronic acid ([14C]HA) incorporation assay. (Castor, C. W., *Arthritis Rheum.* 14, 55–66 (1971).) Synoviocytes were maintained in subconfluent monolayer cultures, infected with purified suspensions of AdRSVIRAP at various multiplicities of infection ("moi") from 102–104 plaque forming unit (pfu)/cell for a period of 4 hours, outgrown, and maintained as confluent monolayer cultures for 7 days post infection.

The rate of transgenic IL-1ra production was determined in the infected synoviocytes at 1, 4, and 7 days post infection. Synoviocytes were washed twice in PBS and then exposed to serum free tissue culture media for a period of 4 hours. Tissue culture supernatants were collected and frozen at −70° C. until use. Synoviocytes were then harvested by trypsinization, washed three times in PBS, pelleted and resuspended in 10 mM TrisCl pH 7.4. Cell lysates were prepared using three cycles of freeze thawing, debris were removed by centrifugation and the lysates were frozen at −70° C. until use. The tissue culture supernatants and cell lysates were then analyzed using an enzyme linked immunoabsorbent assay (ELISA) specific for human IL-1ra (R&D Systems). Table 1 shows that AdRSVIRAP was able to mediate the high level intracellular expression of human IL-1ra with persistence of gene expression for at least 1 week in vitro. In addition, the synoviocytes were able to process and secrete human IL-1ra into the media (Table 2). No significant cytopathic effect was observed in the infected cells, and they continued to grow at rates comparable to uninfected controls and exhibited contact inhibition at confluence.

TABLE 1

In vitro expression of human IL-1ra protein by human synoviocytes infected with AdRSVIRAP

| Virus MOI (pfu/cell)[a] | Days post infection | IRAP[b] |
|---|---|---|
| AdIRAP: $10^2$ | 4 | 83.0 |
| $10^2$ | 7 | 91.7 |
| $10^3$ | 4 | 329.1 |

TABLE 1-continued

In vitro expression of human IL-1ra protein by human synoviocytes infected with AdRSVIRAP

| Virus MOI (pfu/cell)[a] | Days post infection | IRAP[b] |
|---|---|---|
| $10^3$ | 7 | 11,285 |
| $10^4$ | 7 | 26,901 |
| AdlacZ: $10^4$ | 7 | 0.016 |

[a]MOI = mutiplicity of infection, pfu = plague forming units.
[b]IRAP production is expressed as ng/mg of total soluble protein present in cell lysates.

TABLE 2

In vitro secretion of human IL-1ra protein by human synoviocytes infected with AdRSVIRAP

| Virus: MOI (pfu/cell)[a] | Days post infection | IRAP[b] |
|---|---|---|
| AdIRAP: $10^2$ | 1 | 0.01 |
| $10^2$ | 4 | 5.9 |
| $10^2$ | 7 | 5.3 |
| $10^3$ | 1 | 0.35 |
| $10^3$ | 4 | 17.9 |
| $10^3$ | 7 | 13.0 |
| $10^4$ | 1 | 5.2 |
| $10^4$ | 4 | 57.8 |
| $10^4$ | 7 | NA[c] |
| AdlacZ: $10^4$ | 7 | 0.0012 |

[a]MOI = mutiplicity of infection, pfu = plaque forming unit
[b]IRAP production is expressed as ng/mg of total protein/hr present in 10 ml of serum free tissue culture supernatant collected over a period of 4 hours.
[c]NA = not available Duplicate aliquots of the infected cells were harvested 48 hours post infection and total cellular DNA was isolated and used for Southern analysis to determine the transgenic IL-1ra copy number and integrative status of adenoviral DNA. Southern blotting using Bam HI as a restriction enzyme resulted only in the formation of DNA fragments consistent with the known size of the parent adenoviral genome and human IL-1ra cDNA, suggesting that the recombinant adenovirus had not integrated into the host genome. The Southern blot was analyzed using a phospho-imager (Molecular Dynamics) and the information was used to estimate the number of viral genomes/target cell.

Based upon the success of the in vitro experiments, the ability of AdRSVIRAP to mediate transgenic expression of IL-1ra by synoviocytes in vivo was determined using normal rabbit synovium as a target tissue. New Zealand White rabbits 2 kg in weight were used for these experiments, and freshly prepared suspensions of AdRSVIRAP were used for intra-articular injections. Prior to the procedure rabbits were anesthetized with a single intramuscular dose of ketamine/xylazine, and the area surrounding both hind knees was shaved and prepped with povidone/iodine. Using sterile technique and a medial approach, 1 ml of AdRSVIRAP suspension (2.0×1010 pfu/ml) in PBS was infused into the intra-articular space of the right knee.

The left knee was prepared in an identical manner and injected with 1 ml of PBS or 1 ml of the control virus AdBglII. None of the rabbits experienced evidence of clinically relevant arthritis as determined by their ability to ambulate in their cages, serial measurement of articular circumference or as determined by the presence of overlying erythema of the periarticular skin. At 1–4 weeks post infection animals were euthanized with an intravenous overdose of pentobarbital, and the knees were examined for the expression of human IL-1ra.

The hind knees were lavaged with two 1 ml aliquots of PBS and the pooled fluids were frozen at −70° C. until use. The concentration of human IL-1ra in the fluid was determined by ELISA, the total protein concentration was determined using the method of Lowry. See Table 3. The values are recorded as pg of IL-1ra/mg of total protein present in the lavage fluid.

TABLE 3

In vitro expression of human IL-1ra protein by rabbit synovium 1–4 weeks post-infection with AdRSVIRAP IL-1ra (pg/mg total protein)

| Time (weeks) | Right Knee AdRSVIRAP | Left Knee Control |
|---|---|---|
| 1 | 777,742 | 49.4 |
| 2 | 93.6 | 22.4 |
| 3 | 76.8 | 7.1 |
| 4 | 54.3 | 4.8 |

Samples of freshly frozen synovial tissue obtained from the infected rabbits were examined by in situ cRNA hybridization. Because synoviocytes may constitutively express low levels of IL-1ra, or upregulate IL-1ra as a result of adenoviral infection, the specific expression of transgenic human IL-1ra in rabbit synovium was confirmed using $^{35}$S labeled probes specific for human IL-1ra cDNA sequences. Extensive areas of synovium were positive for high level transgene transcription 1 week post infection. However, from 2–4 weeks post infection very few of the infected synoviocytes continued to show active transgene transcription. Samples of synovium infected with AdBglII or AdRSVlacZ or PBS alone showed no increase over background hybridization, and hence no evidence of enhanced endogenous IL-1ra expression or transgenic human IL-1ra expression.

The normal rabbit knee contains little joint fluid, and the rabbits in this series of experiments did not develop joint effusions as a result of the intra-articular infection procedure. Therefore, the amount of transgenic IL-1ra present within the knee joint at the time of sacrifice was determined indirectly by performing a medial arthrotomy followed by sequential lavage with two 1 ml aliquots of PBS. Fluid was collected by aspiration of the joint space, cellular debris removed by centrifugation, and the concentration of human IL-1ra present in pooled lavage fluid determined using ELISA. The results of these experiments are shown in Table 3. Elevated levels of IL-1ra were detected within the knees of rabbits infected with AdRSVIRAP at a dose of 2×1010 pfu/knee for at least 4 weeks post-infection. Peak intra-articular concentrations of IL-1ra were noted 1 week post infection with a significant decline in the measurable levels of IL-1ra present in joint lavage fluid detected at 14 days post infection. A more gradual decline in the levels of intra-articular IL-1ra were observed between 14 and 30 days post infection. The data obtained in this series of experiments was consistent with that obtained by the in situ hybridization studies.

A second group of rabbits injected with a single dose of AdRSVIRAP at a concentration of 1×10$^8$ pfu/ml showed consistent levels of intra-articular IL-1ra expression when examined 1 week post infection, while the levels of IL-1ra expression within knees injected with AdBglII or PBS remained at baseline levels. Results showed that the IL-1ra recovered from the lavage fluid was transgenic in origin and not secondary to induction of endogenous rabbit IL-1ra expression by synovial tissue infected with adenoviruses.

Although the data obtained from in situ cRNA hybridization and ELISA of joint lavage fluid indicated a decline in the number of detectable IL-1ra expressing cells present within infected synovium from 1 to 4 weeks post infection, intra-articular levels of IL-1ra remained elevated for at least 4 weeks post infection. We believe this information is most consistent with the hypothesis that low levels of transgene expression continued for at least 4 weeks post-infection, and that these cells were not readily detected by our sampling methods.

Unlike the exogenous administration of recombinant IL-1ra, our data suggests that recombinant adenoviruses can mediate both the intracellular and extracellular production of IL-1ra, and can thus inhibit IL-1 mediated inflammation via both intracellular and extracellular pathways. In summary, we have shown that recombinant adenoviral vectors can mediate high level expression of human IL-1ra by synovial tissues in vivo.

Although the invention has been described with reference to the presently-preferred embodiments, it should be understood that various modifications can be made without departing from the spirit of the invention. Accordingly, the invention is limited only by the claims that follow.

We claim:

1. A method of reducing an inflammatory response in a joint of a subject comprising:

(a) administering to the joint a therapeutically effect amount of a recombinant adenoviral vector comprising an expression control sequence operatively linked to a gene that encodes an IL-1 receptor antagonist; and     (b) expressing said IL-1 receptor antagonist at a level sufficient to reduce an inflammatory response in said joint.

2. The method of claim 1 wherein said administering step comprises injecting said adenoviral vector into the synovial space of said joint.

* * * * *

UNITED STATES PATENT AND TRADEMARK OFFICE
CERTIFICATE OF CORRECTION

PATENT NO. : 5,747,072  
DATED : May 5, 1998  
INVENTOR(S) : Davidson et al.

Page 1 of 1

It is certified that error appears in the above-identified patent and that said Letters Patent is hereby corrected as shown below:

Column 1,  
Line 3, please insert -- The present invention was supported by grant PO1DK42718 from the National Institutes of Health. The United States Government may have rights in the invention. --.

Column 10,  
Line 29, please delete "14, 55-66" and replace therefor with -- 14:55-66 --

Column 15, claim 1,  
Line 49, please delete "effect" and replace therefor with -- effectively --.

Signed and Sealed this

Twelfth Day of February, 2002

Attest:

JAMES E. ROGAN  
Attesting Officer     Director of the United States Patent and Trademark Office